United States Patent [19]

Finkelstein et al.

[11] Patent Number: 4,837,353
[45] Date of Patent: Jun. 6, 1989

[54] DOPAMINE-β-HYDROXYLASE INHIBITORS

[75] Inventors: Joseph A. Finkelstein, Philadelphia, Pa.; Lawrence I. Kruse, Tewin, England; Thomas B. Leonard, Haverford, Pa.

[73] Assignee: SmithKline Beckman Corporation, Philadelphia, Pa.

[21] Appl. No.: 146,537

[22] Filed: Jan. 21, 1988

Related U.S. Application Data

[62] Division of Ser. No. 29,512, Mar. 24, 1987.

[51] Int. Cl.[4] .................. C07C 101/30; C07C 101/02
[52] U.S. Cl. ........................................ 560/39; 560/41; 560/43; 560/44; 558/410
[58] Field of Search ...................... 560/41, 39, 43, 44; 558/410

[56] References Cited

PUBLICATIONS

Chemical Abstracts, vol. 100, No. 11, Abstract No. 85699r, Mar. 12, 1984, p. 547, (Maier et al.).

*Primary Examiner*—Mary C. Lee
*Assistant Examiner*—Zinna Northington
*Attorney, Agent, or Firm*—Stuart R. Suter; Alan D. Lourie; Janice E. Williams

[57] ABSTRACT

2-(N-Phenylakyl-N-formyl)amino-3-hydroxy-2-propenoic acids are intermediates for mercaptoimidazolecarboxylic acids which are dopamine-β-hydroxylase inhibitors.

2 Claims, No Drawings

DOPAMINE-β-HYDROXYLASE INHIBITORS

This is a division of application Ser. No. 029,512, filed Mar. 24, 1987.

FIELD OF THE INVENTION

This invention relates to novel compounds that inhibit dopamine-β-hydroxylase.

BACKGROUND OF THE INVENTION

In the catecholamine biosynthetic pathway, tyrosine is converted in three steps to norepinephrine (NE). Intermediates are dihydroxyphenylalanine (DOPA) and dopamine (DA). Dopamine is hydroxylated to norepinephrine by dopamine-β-hydroxylase (DBH) in the presence of oxygen and ascorbic acid.

Inhibition of catecholamine activity decreases blood pressure. Weinshilboum, *Mayo Clin. Proc.* 55, 39 (1980), reviews compounds that inhibit catecholamine activity by acting upon adrenergic receptors. Alternatively, the catecholamine biosynthetic pathway can be suppressed at any of the three steps, resulting in reduced NE levels. In addition to producing an antihypertensive effect, inhibitors of NE synthesis are active as diuretics, natriuretics, cardiotonics, and vasodilators. Inhibition of DBH activity can have the added advantage of increasing DA levels, which as reported by Ehrreich et al., "New Antihypertensive Drugs," Spectrum Publishing, 1976, pp. 409-432, has selective vasodilator activity at certain concentrations.

DBH inhibitors also have been shown to reduce or prevent formation of gastric ulcers in rats by Hidaka et al., "Catecholamine and Stress," edit. by Usdin et al., Permagon Press, Oxford, 1976, pp. 159-165 and by Osumi et al., *Japan J. Pharmacol.* 23, 904 (1973).

A number of DBH inhibitors are known. These generally are divided into two classes, namely, metal chelating agents, which bind copper in the enzyme, and phenethylamine analogues. Rosenberg et al., "Essays in Neurochemistry and Neuropharmacology," Vol. 4, ed. by Youdim et al., John Wiley & Sons, 1980, pp. 179-192, and Goldstein, *Pharmacol. Rev.* 18(1), 77 (1966), review DBH inhibitors. The former report that many potent DBH inhibitors have a hydrophobic side chain of size comparable to the aromatic ring of DA, leading the authors to suggest that incorporation of a terminal hydroxyl group on a 4- to 6- carbon side chain on a phenethylalamine analogue may yield potent inhibitors.

Known DBH inhibitors include:

(a) 5-alkylpicolinic acids [See, Suda et al., *Chem. Pharm. Bull.* 17, 2377 (1969); Umezawa et al., *Biochem. Pharmacol.* 19, 35 (1969); Hidaka et al., *Mol. Pharmacol.* 9, 172 (1973); Miyano et al., *Chem. Pharm. Bull.* 26, 2328 (1978); Miyano et al., *Heterocycles* 14, 755 (1980); Claxton et al., *Eur. J. Pharmacol.* 37, 179 (1976))];

(b) BRL 8242 [See Claxton et al., *Eur J. Pharmacol.* 37, 179 (1976)];

(c) 1-alkylimidazole-2-thiols [See, Hanlon et al., *Life Sci.* 12, 417 (1973); Fuller et al., *Adv. Enzyme Regul.* 15, 267 (1976)];

(d) substituted thioureas [See, Johnson et al., *J. Pharmacol. Exp. Ther.* 168, 229 (1969)]; and (e) benzyloxyamine and benzylhydrazine [See, Creveling et al., *Biochim. Biophys. Acta* 64, 125 (1962); Creveling et al., *Biochim. Biophys. Acta* 8, 215 (1962); Van Der Schoot et al., *J. Pharmacol. Exp. Ther.* 141, 74 (1963); Bloom, *Ann. N.Y. Acad. Sci* 107, 878 (1963)].

All the above compounds except benzyloxyamine and benzylhydrazine apparently owe their inhibitory effect to metal chelating properties. Alkyl derivatives of imidazole-2-thiol are more potent, presumably due to non-specific interaction of the alkyl substituent with the enzyme. Benzyloxyamine and benzylhydrazine are phenethylamine analogues which apparently act as competitive inhibitors.

In addtion to the above compounds, Runti et al., *Il Farmaco Ed. Sci.* 36, 260 (1980), report that other fusaric acid derivatives and analogues inhibit DBH. These include phenylpicolinic acid, which has twice the inhibitory activity of fusaric acid, and 5-(4-chlorobutyl) picolinic acid, and others such as substituted amides of fusaric acid and acids and amides of 5-butyroylpicolinic acid, 5-aminopicolinic acid and 5-hydrazinopicolinic acid, and derivatives thereof.

Hidaka et al., *Molecular Pharmacology,* 9, 172-177 (1972) report that 5-(3,4-dibromobutyl)picolinic acid and 5-(dimethyldithiocarbamoylmethyl)picolinic acid are DBH inhibitors.

Bupicomide, 5-(n-butyl)picolinamine, is reported by Ehrreich et al., "New Antihypertensive Drugs", Spectrum Publications, 1976, pg. 409-432, to be a DBH inhibitor that has antihypertensive activity.

In European Patent Application No. 125,033 (published Nov. 14, 1984) a series of 1-phenyl and 1-phenylalkylimidazole compounds having a mercapto or alkylthio group in the 2-position are disclosed. These compounds are described as having DBH inhibiting activity.

U.S. Pat. No. 4,487,761 describes several methylpyridine derivatives isolated from the fermentation broth of a strain of *Streptoverticillium.* These compounds inhibit DBH activity.

U.S. Pat. No. 4,532,331 describes various 1-benzyl-2-aminomethyl imidazole derivatives that inhibit DBH acitivy and includes pharmaceutical compositions containing these derivatives and methods of using these derivatives to inhibit DBH activity.

Non-specific, often toxic effects to known DBH inhibitors have obviated clinical use of these compounds. Fusaric acid, for example, is hepatotoxic. See, for example, Teresawa et al., *Japan. Cir. J.* 35, 339 (1971) and references cited therein. Presumably, the picolinic acid structure interacts with a number of metalloproteins and enzymes non-specifically to produce the observed side effects.

SUMMARY OF THE INVENTION

The present invention resides in the discovery that DBH is inhibited by substituted 1-aralkyl-2-mercaptoimidazole-5-carboxylic acid and substituted 1-aralkyl-2-mercaptoimidazole-5-aminoalkylamide compounds and their 2-alkyl mercapto derivatives. These compounds are potent and produce prolonged DBH inhibition.

Presently preferred compounds of the invention and compounds included in the pharmaceutical compositions and used in the methods of the invention include:
1-(3,5-difluorobenzyl)-2-mercaptoimidazole-5-carboxylic acid; and
N-(2-aminoethyl)-1-(3,5-difluorobenzyl)-2-mercaptoimidazole-5-carboxamide.

In a further aspect of the invention there are provided novel intermediates useful in preparing substituted 1- aralkyl-2-mercaptoimidazole-5-carboxylic acid and substituted 1-aralkyl-2-mercaptoimidazole-5-aminoalkylamide compounds.

The invention also is a method of inhibiting DBH activity in mammals, including humans, which comprises administering internally to a subject an effective amount of a substituted 1-aralkyl-2-mercaptoimidazole-5-carboxylic acid and substituted 1-aralkyl-2-mercaptoimidazole-5-aminoalkylamide compounds.

Included in the present invention are pharmaceutical compositions comprising compounds useful in the method of the invention and a pharmaceutical carrier.

DETAILED DESCRIPTION OF THE INVENTION

The presently invented compounds that inhibit DBH have the following formula:

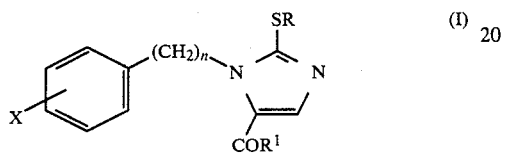

in which:

X is H, F, Cl, Br, I, $C_{1-4}$alkyl, CN, $NO_2$, $SO_2NH_2$, COOH, OH, CHO, $C_{1-4}$alkoxy, $CH_2OH$, $CF_3$, $SO_2CH_3$, $SO_2CF_3$, or $CO_2C_aH_{2a+1}$ wherein a is 1-5, or any accessible combination thereof of up to 5 substituents;

n is 0-5;

R is hydrogen or $C_{1-4}$alkyl; and $R^1$ is OH or $NHC_{1-4}alkylNH_2$; or any pharmaceutically acceptable salt or hydrate thereof.

As used herein, "accessible combination thereof" means any combination of the substituents that is available by chemical synthesis and is stable. $C_{1-4}$alkyl means a straight or branched chain alkyl having from 1 to 4 carbon atoms.

It is intended that Formula I includes the tautomer of the compounds in which R is hydrogen, that is, compounds having the above formula wherein the imidazole moiety has either of the below formulae:

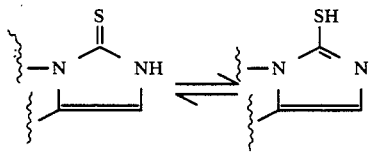

The compounds of Formula I in which n is 1 are prepared from corresponding benzaldehydes by processes such as shown in Schemes I and II, below. The starting benzaldehydes are known and described in published references or can be obtained readily by known methods. In Schemes I and II, X and R are as defined in Formula I, $X^1$ is chloro, bromo, or iodo, and $R^2$ is $C_{1-4}$alkyl.

SCHEME I

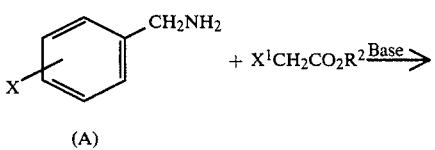

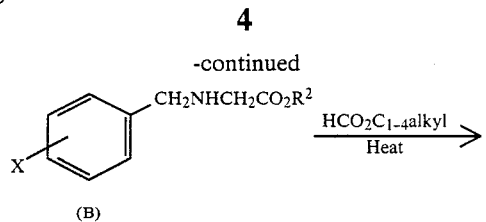

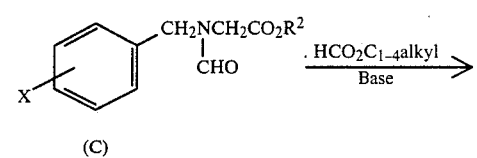

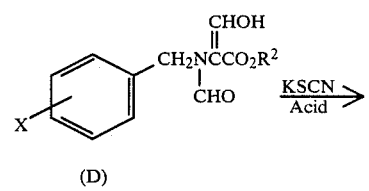

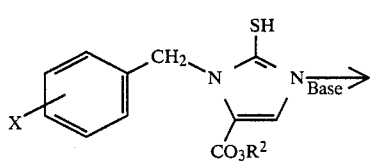

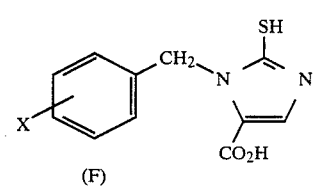

Scheme I illustrates formation of Formula I compounds in which $R^1$ is OH. According to Scheme I, a benzylamine (A) substituted as in the desired Formula I compound is reacted with a haloacetic acid ester, preferably in which X is chloro and $R^2$ is methyl, in the presence of base such as a trialkylamine, potassium carbonate, sodium carbonate, or, preferably, triethylamine, to yield a formula (B) compound. Formula (C) compounds then are prepared by heating at 40° to 95° C., preferably 65°-70° C., a formula (B) compound with a $C_{1-4}$alkyl formic acid ester, or, preferably, formic acid. Treatment of formula (C) compounds with a $C_{1-4}$alkyl formic acid ester and a strong base such as sodium, potassium, or lithium salts of $C_{1-4}$alkoxides, preferably sodium methoxide yields compounds of formula (D). Formula (E) compounds, then are synthesized by reaction of formula (D) compounds with acidic thiocyanate. Heating formula (E) compounds with a strong acid or base, preferably sodium hydroxide, yields formula (F) compounds which are Formula (I) compounds in which $R^1$ is OH.

Formula I compounds in which n is O are prepared using the Scheme I process by replacing the starting benzylamines with substituted anilines which are known and readily obtainable. Formula I compounds in which n is 2 to 5 similarly are prepared by replacing the benzylamines with substituted phenyl$C_{2-5}$alkylamines which also are known and readily obtainable.

SCHEME II

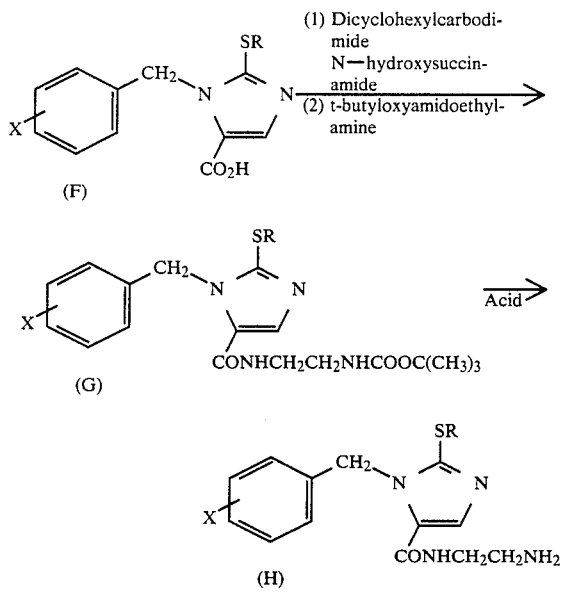

Scheme II outlines synthesis of Formula I compounds in which $R^1$ is $NHC_{1-4}alkylNH_2$ from Formula I compounds in which $R^1$ is OH prepared according to Scheme I. According to Scheme II, N-hydroxysuccinimide and dicyclohexylcarbodiimide are added to a formula (F) compound in an inert organic solvent, preferably tetrahydrofuran, followed by addition of t-butyloxyamidoethylamine to produce formula (G) compounds. Treating the formula (G) compounds with strong acid such as hydrochloric, hydrobromic, acetic, or, preferably, formic, yields formula (H) compounds which are Formula I compounds in which $R^1$ is $NHCH_2CH_2NH_2$. Formula I compounds wherein $R^1$ is other $NHC_{1-4}alkylNH_2$ are prepared using Scheme II by replacing t-butyloxamidoethylamine with appropriate t-butyloxamide$C_{1-4}$alkylamines.

Compounds of the invention in which R is $C_{1-4}$alkyl are prepared by alkylating the corresponding Formula (I) compound wherein R is hydrogen with, for example, methyl iodide in methanol by known procedures. Other alkyl halides such as methyl bromide or methyl chloride, in appropriate solvents, can be substituted for methyl iodide. Further, the compounds in which R is an alkyl group other than methyl are prepared by reacting the corresponding Formula (I) compound with an alkyl halide, such as butyl iodide, in an appropriate solvent to yield the desired compound of the invention.

In preparing the presently invented compounds of Formula I, novel intermediate compounds of the following formula were synthesized:

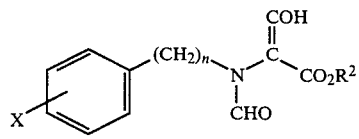

in which:

X and n are as defined in Formula I and $R^2$ is as defined in Scheme I.

Intermediates of the following formula also were synthesized:

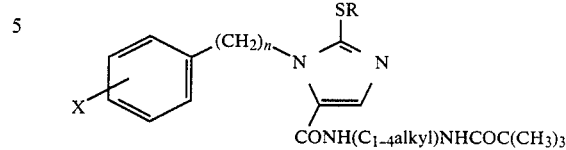

in which X, n, and R are as defined in Formula I.

The pharmaceutically acceptable salts of compounds of the invention are formed, when appropriate, with strong or moderately strong organic or inorganic acids by methods known to the art. For example, the base is reacted with an inorganic or organic acid in an aqueous miscible solvent such as ethanol with isolation of the salt by removing the solvent. Alternatively, when the acid is soluble in an aqueous immiscible solvent, such as ethyl ether or chloroform, the desired salt separates directly when base is added or is isolated by removing the solvent. Exemplary of the salts which are included in this invention are maleate, fumarate, lactate, oxalate, methanesulfonate, ethanesulfonate, benzenesulfonate, tartrate, citrate, hydrochloride, hydrobromide, sulfate, phosphate, quinate, and nitrate salts. Pharmaceutically acceptable salts of compounds of the invention also are formed, when appropriate, with strong or moderately strong bases by known methods. Such salts include the sodium, potassium, lithium, calcium, magnesium, trialkylamine, dialkylamine, alkylamine, ammonium, and trihydroxymethylamine salts.

Because the Formula I compounds inhibit DBH activity, they have therapeutic value as diuretic, natriuretic, cardiotonic, antihypertensive, and vasodilator agents, as well as antiulcerogenic and anti-Parkinsonian agents. Listed in Table I are the compounds of the invention that were tested for in vitro DBH inhibition by a standard procedure for assaying conversion of tyramine to octopamine in the presence of DBH. J. J. Pisano, et al., *Biochim. Biophys. Acta*, 43, 566–568 (1960). Octopamine was assayed following sodium periodate oxidation to p-hydroxybenzaldehyde by measuring spectrophotometric absorbance at 330 nm. In Table I, inhibition is given in molar concentration of compound at which DBH activity was halved ($IC_{50}$). Fusaric acid, by this test was found to have an $IC_{50}$ of $8 \times 10^{-7}$M.

TABLE I

| Compound | DBH $IC_{50}$ |
|---|---|
| 1-(3,5-Difluorobenzyl)-2-mercapto-imidazole-5-carboxylic acid | $1.0 \times 10^{-4}$ M |
| N—(2-aminoethyl)-1-(3,5-difluoro-benzyl)-2-mercaptoimidazole-5-carboxamide, formate | $3.4 \times 10^{-7}$ M |

Further, spontaneously hypertensive rats were treated with a suspension or solution of N-(2-aminoethyl)-1-(3,5-difluorobenzyl)-2-mercaptoimidazole-5-carboxamid formate at a dose of 50 mg/kg intraperitoneally, and mean arterial blood pressure was monitored for 260 minutes using indwelling cannulae in the tail arteries. When compared to vehicle-treated controls, the animals treated with the compound of the invention exhibited significant blood pressure reductions within 30 minutes following treatment, and blood pressure remained decreased when monitoring was terminated.

The compounds of Formula I can be incorporated into convenient pharmaceutical dosage forms such as capsules, tablets, or injectable preparations. Solid or liquid pharmaceutical carriers can be employed. Solid carriers include, starch, lactose, calcium sulfate dihydrate, terra alba, sucrose, talc, gelatin, agar, pectin, acacia, magnesium stearate, and stearic acid Liquid carriers include syrup, peanut oil, olive oil, saline, and water. Similarly, the carrier or diluent may include any prolonged release material, such as glyceryl monostearate or glyceryl distearate, alone or with a wax. The amount of solid carrier varies widely but, preferably, will be from about 25 mg to about 1 g per dosage unit. When a liquid carrier is used, the preparation will be in the form of a syrup, elixir, emulsion, soft gelatin capsule, sterile injectable liquid such as an ampoule, or an aqueous or nonaqueous liquid suspension.

The pharmaceutical preparations are made following conventional techniques of a pharmaceutical chemist involving mixing, granulating and compressing, when necessary, for tablet forms, or mixing, filling, and dissolving the ingredients, as appropriate, to give the desired oral or parental products.

The method of this invention of inhibiting DBH activity in mammals, including humans, comprises administering internally to a subject in need of such inhibition an effective DBH inhibiting amount of a compound of Formula I.

Doses of the present compounds of Formula I in a pharmaceutical dosage unit as described above will be an efficacious, nontoxic quantity selected from the range of 0.1–100 mg/kg of active compound, preferably 0.1–50 mg/kg. The selected dose is administered to a human patient in need of DBH inhibition from 1–6 times daily, orally, rectally, by injection, or continuously by infusion. Oral dosage units for human administration preferably contain from 1 to 500 mg of active compound. Parenteral administration, which uses lower dosages is preferred. Oral administration, at higher dosages, however, also can be used when safe and convenient for the patient.

The following examples are illustrative of preparation of Formula I compounds. The examples are not intended to limit the scope of the invention as defined hereinabove and as claimed below.

EXAMPLE 1

1-(3,5-Difluorobenzyl)-2-mercaptoimidazole-5-carboxylic acid (i) 3,5-Difluorobenzylamine A slurry of Raney nickel in methanol was added to a solution of 3,5-difluorobenzonitrile (12.0 g, 0.0863 mole) in methanol (100 ml) saturated with ammonia and th emixture was hydrogenated for 2.5 hours at 50 pounds pressure. The solution was decanted from the catalyst and the catalyst washed four times with methanol and decanted. The combined decanted solvent was evaporated and the residue dissolved in ethyl acetate and extracted twice with 1N hydrochloric acid (50 ml). The acid solution was made basic with 10% sodium hydroxide and extracted with three portions of ethyl acetate. The ethyl acetate was washed with water, brine, dried over sodium sulfate and the solvent removed to give 3,5-difluorobenzylamine as an oil (12.3 g, 100%).

(ii) N-(3,5-Difluorobenzyl)glycine methyl ester

A solution of 3,5-difluorobenzylamine prepared as above (12.3 g, 0.0863 mole), methyl chloroacetate (7.6 ml, 0.0863 mole) and triethylamine (12.0 ml, 0.0863 mole) in dry dimethylformamide (85 ml) was heated at 60° C. for 3 hours. The mixture was diluted with an equal volume of ether and the triethylamine hydrochloride filtered. The filtrate was concentrated under vacuum, the resultant oil triturated with ethyl acetate, and the solution decanted from a small amount of residual oil. The solvent was removed and the product was purified by flash chromatography (silica) by eluting with hexane-ethyl acetate (70:30) to give N-(3,5-difluorobenzyl)glycine methyl ester as an oil (7.61 g, 41%).

(iii) N-formyl-3,5-difluorobenzyl)glycine methyl ester

A solution of N-3,5-(difluorobenzyl) glycine methyl ester (7.61 g, 0.0352 mole) prepared as above and formic acid (1.33 ml, 0.0352 mole) was heated at reflux in xylene (60 ml) with azeotropic removal of water for 2.5 hours and the solvent was removed under vacuum to give N-formyl-(3,5-difluorobenzyl)glycine methyl ester as an oil (8.50 g, 99%).

(iv) 1-(3,5-Difluorobenzyl)-2-mercaptoimidazole-5-carboxylic acid methyl ester

Methanol (1.54 ml, 0.0381 mole) was added to a suspension of sodium (0.876 g, 0.0381 mole) in dry tetrahydrofuran and the mixture stirred for 30 minutes. A solution of N-formyl-(3,5-difluorobenzyl) glycine methyl esters (8.50 g, 0.0349 mole) prepared as above in methyl formate (6.57 ml, 0.107 mole) was added dropwise to the sodium methoxide solution with cooling at 10° to 15° C. and the resulting mixture was stirred overnight at room temperature. The solvent was removed under vacuum and the residue was diluted with 100 ml water-methanol (1:1). The solution was treated with activated carbon, filtered and cooled in ice. Hydrochloric acid (12 N, 6.4 ml) and a solution of potassium thiocyanate (4.25 g, 0.0437 mole) in a minimum amount of water were added and the resulting solution was heated at 65°–70° C. for 24 hours. The solution was treated with activated carbon, filtered, and the solvent was removed under vacuum until a precipitate formed. The mixture was cooled in ice and the product filtered and washed with a mixture of methanol-water. The product was triturated with ethanol, filtered and dried to give 1-(3,5-difluorobenzyl)-2-mercaptoimidazole-5-carboxylic acid methyl ester, m.p.: 177°–178° C. (6.75 g, 68%).

(v) 1-(3,5-Difluorobenzyl)-2-mercaptoimidazole-5-carboxylic acid

A solution of sodium hydroxide (2.70 g, 0.674 mole) in water (110 ml) was added to 1-(3,5-difluorobenzyl)-2-mercaptoimidazole-5-carboxylic acid methyl ester prepared as above (6.39 g, 0.0225 mole) and the resulting solution was stirred for 2 hours. The solution was cooled in ice, acidified to pH 2 with 3N hydrochloric acid, and the product was filtered and dried. The product was recrystallized from ethanol-water and dried to give 1-(3,5-difluorobenzyl)-2-mercapto-imidazole-5-carboxylic acid, m.p.: 240°–241° C. (5.66 g, 93%).

EXAMPLE 2

N-(2-Aminoethyl)-1-(3,5-diflurobenzyl)-2-mercaptoimidazole-5-carboxamide (i) N-(t-Butyloxycarbonylaminoethyl)-1-(3,5-diflurobenzyl)-2-mercaptoimidazole-5-carboxamide To a solution of 1-(3,5-difluorobenzyl)-2-mercaptoimidazole-5-carboxylic acid prepared as in Example 1 (1.90 g, 7.02 mmoles) in tetrahydrofuran (15 ml) was added N-hydroxysuccinimide (0.888 g, 7.72 mmole)

followed by dropwise addition of dicyclohexylcarbodiimide (1.45 g, 7.02 mmole) in tetrahydrofuran (25 ml). A solution of t-butyloxyaidoethylamine hydrochloride (1.38 g, 7.02 mmole) and triethylamine (2.94 ml, 21 mmole) in tetrahydrofuran (50 ml) was added in portions and the mixture stirred for 2 hours. The reaction mixture was filtered and the solvent removed under vacuum. The residue was dissolved in ethyl acetate, filtered, and the filtrate was washed with water, dilute hydrochloric acid, 5% sodium bicarbonate and brine. The solution was dried and the solvent removed under vacuum. The resulting oil was triturated with ether, and the product was filtered and dried to give N-(t-butyloxycarbonylaminoethyl)-1-(3,5-diflurobenzyl)-2-mercaptoimidazole-5-car m.p.: 178°–179° C. (1.84 g, 64%).

(ii) N-(2-Aminoethyl)-1-(3,5-difluorobenzyl)-2-mercaptoimidazole-5-carboxamide, formate A solution of N-(t-butyloxycarbonylaminoethyl)-1-(3,5-diflurobenzyl)-2-mercaptoimidazole-5-carboxamide (1.29 g, 3.13 mmole) prepared as above in 98% formic acid (40 ml) was stirred under an argon atmosphere for 3 hours and the solvent was removed under vacuum. The resulting oil was triturated with ether, and the product was filtered and dried to give N-(2-aminoethyl)-1-(3,5-difluorobenzyl)-2-mercaptoimidazole-5-carboxamide, formate, m.p.: 195°–196° C. (0.630 g, 56%).

EXAMPLE 3

1-(3,5-Difluorobenzyl)-2-methylmercaptoimidazole-5-carboxylic acid

Reaction of 1-(3,5-difluorobenzyl)-2-mercaptoimidazole-5-carboxylic acid prepared as in Example 1 with methyl iodide and sodium methoxide in methanol by standard techniques yields 1-(3,5-diflurobenzyl)-2-methylmercaptoimidazole-5-carboxylic acid.

EXAMPLE 4

1-(3,5-Difluorophenyl-3-propyl)-2-mercaptoimidazole-5-carboxylic acid

The process of Example 1 wherein 3,5-difluorobenzylnitrile is replaced by 3,5-difluorophenyl-3-propylnitrile yields 1-(3,5-difluorophenyl-3-propyl)-2-mercaptoimidazole-5-carboxylic acid.

EXAMPLE 5

1-(3-Methoxybenzyl)-2-mercaptoimidazole-5-carboxylic acid

The process of Example 1 in which 3,5-difluorobenzonitrile is replaced by 3-methoxybenzonitrile yields 1-(3-methoxybenzyl)-2-mercaptoimidazole-5-carboxylic acid.

EXAMPLE 6

1-(3-Hydroxymethylbenzyl)-2-mercaptoimidazole-5-carboxylic acid

The process of Example 1 wherein 3,5-difluoro-benzonitrile is replaced by 5-hydroxymethylbenzonitrile yields 1-(5-hydroxymethylbenzyl)-2-mercaptomidazole-5-carboxylic acid.

EXAMPLE 7

1-(3-Acetoxybenzyl)-2-mercaptoimidazole-5-carboxylic acid

The process of Example 1 wherein 3-acetoxybenzonitrile replaces 3,5-diflurobenzonitrile yields 1-(3-acetoxybenzyl)-2-mercaptoimidazole-5-carboxylic acid.

EXAMPLE 8

1-(3-Cyanobenzyl)-2-mercaptoimidazole-5-carboxylic acid

The process of Example 1 wherein 3,5-difluorobenzonitrile is replaced by 3-cyanobenzonitrile yields 1-(3-cyanobenzyl)-2-mercaptoimidazole-5-carboxylic acid.

EXAMPLE 9

N-(2-Amino-n-butyl)-1-(3,5-difluorobenzyl)-2-mercaptoimidazole-5-carboxamide

The process of Example 2 in which t-butyloxyamidoethylamine is replaced by 2-(t-butyloxycarbonylamino)-n-butylamine yields N-(2-amino-n-butyl)-1-(3,5-difluorobenzyl-2-mercaptoimidazole-5-carboxamide.

EXAMPLE 10

An oral dosage form for administering the presently invented compounds is produced by screening, mixing, and filling into hard gelatin capsules the ingredients in the proportions shown in Table III, below.

TABLE III

| Ingredients | Amounts |
| --- | --- |
| 1-(3,5-Difluorobenzyl)-2-mercaptoimidazole-5-carboxylic acid | 50 mg |
| magnesium stearate | 5 mg |
| lactose | 75 mg |

EXAMPLE 11

The sucrose, calcium sulfate dihydrate, and Formula I compound shown in Table IV below, are mixed and granulated in the proportions shown with a 10% gelatin solution. The wet granules are screened, dried, mixed with the starch, talc and stearic acid, screened and compressed into a tablet.

TABLE IV

| Ingredients | Amounts |
| --- | --- |
| N—(2-Aminoethyl)-1-(3,5-difluorobenzyl)-2-mercaptoimidazole-5-carboxamide, formate | 100 mg |
| calcium sulfate dihydrate | 150 mg |
| sucrose | 20 mg |
| starch | 10 mg |
| talc | 5 mg |
| stearic acid | 3 mg |

EXAMPLE 12

N-(2-Aminoethyl)-1-(3,5-difluorobenzyl)-2-mercaptoimidazole-5-carboxamide, formate, 75 mg, is dispersed in 25 ml of normal saline to prepare an injectable preparation.

While the preferred embodiments of the invention are illustrated by the above, it is to be understood that the invention is not limited to the precise instructions herein disclosed and that the right to all modifications coming within the scope of the following claims is reserved.

What is claimed is:

1. A compound represented by the formula:

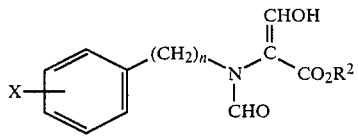

in which:
X is H, F, Cl, Br, I, $C_{1-4}$alkyl, CN, $NO_2$, $SO_2NH_2$, COOH, OH<CHO, $C_{1-4}$alkoxy, $CH_2OH$, $CF_3$, $SO_2CH_3$, $SO_2CF_3$, or $CO_2C_aH_{2a+1}$ wherein a is 1 to 5, or any accessible combination thereof of up to 5 substituents;
$R^2$ is $C_{1-4}$alkyl; and
n is 1-5.

2. A compound of claim 1 wherein X represents 3,5-difluoro, $R_2$ is methyl and n is 1, said compound being methyl 2-[N-(3,5-difluorobenzyl)-N-formyl]amino-3-hydroxy2-propenoate.

* * * * *